| United States Patent [19] | [11] | 4,423,051 |
|---|---|---|
| Shepherd | [45] | Dec. 27, 1983 |

[54] 4-[(CYCLOALKYL OR CYCLOALKENYL SUBSTITUTED) AMINO, ALKYLAMINO OR ALKENYLAMINO]BENZOIC ACIDS, SALTS AND DERIVATIVES THEREOF

[75] Inventor: Robert G. Shepherd, South Nyack, N.Y.

[73] Assignee: American Cyanamid Company, Stamford, Conn.

[21] Appl. No.: 285,206

[22] Filed: Jul. 20, 1981

Related U.S. Application Data

[62] Division of Ser. No. 137,199, Apr. 4, 1980, abandoned, which is a division of Ser. No. 881,457, Feb. 27, 1978, Pat. No. 4,227,014.

[51] Int. Cl.$^3$ .................. A61K 31/44; C07D 309/12; C07D 213/55; C07C 101/62
[52] U.S. Cl. .................................. 424/263; 546/300; 549/420; 560/48; 424/310; 424/283
[58] Field of Search .......................... 560/48; 546/300; 424/310, 263, 283; 549/420

[56] References Cited

U.S. PATENT DOCUMENTS

| 4,243,609 | 1/1981 | Shepherd | 564/91 |
| 4,272,546 | 6/1981 | Shepherd | 424/310 |
| 4,310,545 | 1/1982 | Shepherd | 424/310 |
| 4,348,399 | 9/1982 | Shepherd | 424/263 |
| 4,350,822 | 9/1982 | Albright et al. | 560/45 |

*Primary Examiner*—Alan L. Rotman
*Attorney, Agent, or Firm*—Robert P. Raymond

[57] ABSTRACT

This disclosure describes novel 4-[(cycloalkyl or cycloalkenyl substituted)amino, alkylamino or alkenylamino]-benzoic acids, salts and derviatives of these such as cycloalkylamino, cycloalkenylamino, cycloalkyl-alkylamino, cycloalkyl-alkenylamino, cycloalkenyl-alkylamino, and cycloalkyl-cycloalkylamino benzoic acids and derivatives and suitable salts of these; these compounds are useful as hypolipidemic and antiatherosclerotic agents.

30 Claims, No Drawings

4-[(CYCLOALKYL OR CYCLOALKENYL SUBSTITUTED) AMINO, ALKYLAMINO OR ALKENYLAMINO]BENZOIC ACIDS, SALTS AND DERIVATIVES THEREOF

This is a division of application Ser. No. 137,199 filed Apr. 4, 1980, now abandoned, which in turn is a division of application Ser. No. 881,457 filed Feb. 27, 1978, now U.S. Pat. No. 4,227,014.

BRIEF SUMMARY OF THE INVENTION

This invention deals with 4-[(cycloalkyl or cycloalkenyl substituted)amino, alkylamino, or alkenylamino]-benzoic acids, salts and derivatives of these of the formula:

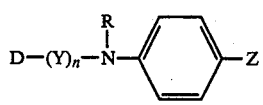

(Formula I)

wherein Z is a moiety of the formula:

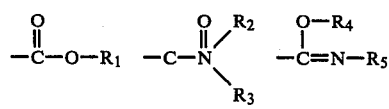

wherein $R_1$ is selected from the group consisting of hydrogen, $C_1$-$C_6$ alkyl, loweralkoxyloweralkyl, diloweralkylaminoloweralkyl, (mono- or polyhydroxy)loweralkyl, allyl, 2,3-epoxypropyl, substituted or unsubstituted-(phenyl, benzyl, or 3-pyridyl), pyridylmethyl, (mono- or polycarboxy)loweralkyl, (mono- or polycarboxy)hydroxyloweralkyl, 2-tetrahydropyranyl; $R_2$ is selected from the group consisting of hydrogen, carboxy loweralkyl, carboalkoxy loweralkyl, loweralkanoyl, loweralkanesulfonyl, arylsulfonyl, sodium sulfo loweralkyl, sulfoloweralkyl, loweralkenyl, loweralkynyl, and aryl loweralkyl; $R_3$ is selected from the group consisting of loweralkyl, hydroxy, loweralkoxy, haloloweralkyl, phenyl, carboxyphenyl, chlorophenyl, sodium sulfophenyl, 3-pyridyl, pyridyl loweralkyl, (mono- and polyhydroxy)loweralkyl, ω-loweralkoxy loweralkyl, ω-di(loweralkyl)aminoloweralkyl, ω-piperidino loweralkyl, ω-pyrrolidino lowerhydroxyalkyl, amino, loweralkanoylamino, loweralkanesulfonylamino, N-piperidyl, arylsulfonylamino, p-toluenesulfonylamino and 4-loweralkyl-1-piperazino; $R_2$ and $R_3$ taken together with the assoicated nitrogen is selected from the group consisting of pyrrolidino, piperidino, morpholino, hexamethyleneimino, loweralkylpiperidino, 4-loweralkyl-1-piperazino, 4-phenylpiperazino, 3-pyrrolinyl, $\Delta^3$-piperidino, 4-(carboethoxy or carboxy)-3-thiazolidinyl, and 4-(carboethoxy)-3-oxazolidinyl; $R_4$ and $R_5$ are the same or different and are selected from the group consisting of loweralkyl, hydroxy loweralkyl, polyhydroxy loweralkyl, carboxy loweralkyl, sulfoloweralkyl, sodium sulfoloweralkyl, and, when taken together, lower alkylene; R is selected from the group consisting of hydrogen, or a group convertible in vivo thereinto, such as methyl, carboxymethyl, acetyl, succinyl, 1-(sodium sulfo)loweralkyl, 1-(sodium sulfo)-polyhydroxyalkyl and 1,3-bis-(sodium sulfo)aralkyl; and, when n is 1

Formula I(A) Y is a divalent radical selected from the group consisting of branched or unbranched $C_1$-$C_{13}$ alkylene or alkenylene and is either unsubstituted or substituted with at least one $C_1$-$C_{C4}$ alkyl; D is a moiety selected from the group consisting of $C_3$-$C_8$ cycloalkyl which is either unsubstituted or substituted with at least one $C_1$-$C_{13}$ alkyl, a $C_5$-$C_7$ cycloalkyl, or a decahydronaphthyl group; with the proviso that D is not an unsubstituted cyclopropyl nor a cyclopropyl substituted with at least one $C_1$ to $C_{13}$ alkyl, or Formula I(B) Y is a divalent radical selected from the group consisting of branched or unbranched $C_1$-$C_{13}$ alkylene or alkenylene; and is either unsubstituted or substituted with at least one $C_1$-$C_2$ alkyl;

and D is a moiety selected from the group consisting of $C_4$-$C_9$ cycloalkenyl and is either unsubstituted or substituted with at least one $C_1$-$C_{13}$ alkyl group; and $C_5$-$C_8$ cycloalkyl unsubstituted or substituted with at least one methylene moiety, and/or at least one $C_1$-$C_{13}$ alkyl;

and when n is 0,

Formula I(C) D is a moiety selected from the group consisting of $C_4$-$C_7$ cycloalkyl and is either unsubstituted or substituted with at least one $C_4$-$C_7$ cycloalkyl, and decahydronaphthalene unsubstituted or substituted with at least one $C_1$ to $C_4$ alkyl; or Formula I(D) D is selected from the group consisting of $C_4$-$C_{16}$ cycloalkyl substituted with at least one $C_1$-$C_5$ alkyl; or Formula I(E) D is a moiety selected from the group consisting of $C_4$-$C_{17}$ cycloalkenyl which is either unsubstituted or substituted with at least one $C_1$-$C_4$ alkyl, and $C_4$-$C_{10}$ cycloalkyl substituted with a moiety selected from the group consisting of methylene, ethylidene, and isopropylidene and/or at least one $C_1$-$C_4$; with the proviso that the sum of the number of carbon atoms contained in D and Y in Formula I shall not exceed twenty; and the pharmaceutically acceptable acid-addition and cationic salts of the above.

The loweralkyl, loweralkenyl, loweralkynyl, loweralkoxy, loweralkanoyl, and loweralkanesulfonyl groups herein contain 1 to 6 carbon atoms and may be branched or unbranched. The number of hydroxyl groups in the polyhydroxy compounds herein are from 2 to 4 hydroxy groups. The number of carboxyl groups in the polycarboxy compounds herein are from 2 to 4 carboxyl groups.

Preferred compounds of Formula I are those compounds wherein R, Y and D are as previously defined and Z is

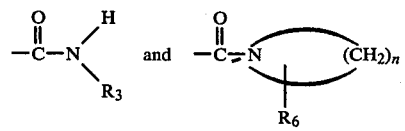

wherein $R_3$ is a $C_2$-$C_4$ alkyl group unsubstituted or substituted with at least one hydroxyl group, $-CH_2-CH=CH_2$, $-CH_2-C\equiv CH$, $-CH_2CH_2SO_3H$, $-(CH_2)_m-COOR_7$ wherein m is 2-4 and $R_7$ is hydrogen or a $C_1$-$C_3$ alkyl group,

wherein $R_8$ is phenyl or a $C_1$-$C_3$ alkyl group, $-SO_2R_9$ wherein $R_9$ is a $C_1$-$C_3$ alkyl or phenyl or p-tolyl group, —OH, OCH$_3$ and OCH$_2$CH$_3$, NHSO$_2$-R$_8$ wherein R$_8$ is a previously defined, and wherein n is one of the integers 4, 5 and 6 and R$_6$ is hydrogen or represents at least one methyl group.

Additional preferred embodiments of the compounds of Formula I are those wherein R, Y and D are as previously defined and Z is the moiety

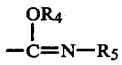

wherein R$_4$ and R$_5$ are as previously defined.

Preferred compounds of Formulas IA, IB, IC, ID and IE are those wherein Z is the moiety COOR$_1$ wherein R$_1$ is hydrogen, C$_1$-C$_6$ alkyl, a C$_1$-C$_6$ alkyl substituted with one or more carboxyl groups, a C$_1$-C$_3$ alkyl substituted with at least one hydroxyl or carboxyl group, a C$_1$-C$_3$ alkyl substituted with a dialkylamino moiety or a C$_1$-C$_4$ dialkylamino moiety and a hydroxyl group, a C$_1$-C$_3$ alkyl substituted with a polymethyleneimino (ring size 5-8) and a hydroxyl group; a C$_1$-C$_3$ alkyl substituted with a dialkylamino moiety and a hydroxy group; a benzyl group, a benzyl group optionally substituted with at least one fluorine, chlorine, bromine, iodine, or carboxyl group, a phenyl moiety, a phenyl group optionally substituted with at least one chlorine, bromine, iodine, fluorine or carboxyl group, and 3-pyridyl.

More preferred compounds of the Formula IA are those

Most preferred compounds of the Formula IA are those wherein Y is a divalent radical selected from those consisting of straight-chain C$_1$-C$_{13}$ alkylene; and still more preferred are the compounds of Formula IA wherein D is a moiety selected from the group consisting of C$_5$ to C$_8$ cycloalkyl. The most preferred compounds of Formula IA are those where Y is a divalent radical selected from the group consisting of straight chain C$_6$ to C$_8$ alkylene.

More preferred compounds of Formula IB are those where D is selected from the group consisting of C$_5$-C$_8$ cycloalkenyl unsubstituted or substituted with at least one C$_1$-C$_2$ alkyl and Y is a divalent radical selected from the group consisting of C$_1$-C$_{13}$ alkylene; and those compounds wherein Y is a divalent radical selected from the group consisting of C$_4$-C$_{13}$ alkylene and/or D is C$_5$ or C$_6$ cycloalkyl are even more preferred. Additionally preferred embodiments of compounds of Formula IB are those where D is selected from the group consisting of C$_5$ to C$_8$ cycloalkyl substituted with a methylene moiety and/or at least one C$_1$-C$_2$ alkyl, and Y is

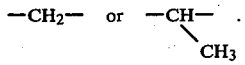

Preferred embodiments of the compounds of Formula IC are those where D is selected from the group consisting of C$_5$-C$_6$ cycloalkyl which is either unsubstituted or substituted with at least one C$_5$-C$_6$ cycloalkyl, and decahydronapthyl unsubstituted or substituted with at least one C$_1$-C$_4$ alkyl.

More preferred compounds of Formula ID are those where D is selected from the group consisting of C$_4$-C$_{16}$ cycloalkyls which may be unsubstituted or substituted with at least one C$_{1-5}$ alkyl and most preferred are those where D is selected from the group consisting of C$_5$ to C$_{12}$ cycloalkyl.

More preferred compounds of Formula IE are those where D is C$_4$-C$_{17}$ cycloalkenyl or C$_4$-C$_8$ cycloalkenyl substituted with at least one C$_{1-4}$ alkyl group; and even more preferred of these is where D is C$_5$-C$_{17}$ cycloalkenyl and more preferred of these is where D is C$_6$ to C$_{15}$ cycloalkenyl. Other preferred compounds of Formula IE are those where D is C$_4$-C$_{10}$ cycloalkyl substituted with methylene, ethylidene or isopropylidene. Of these the most preferred are those in which D is a C$_5$-C$_{10}$ cycloalkyl substituted with a methylene.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-[(cycloalkyl or cycloalkenyl substituted)amino, alkylamino or alkenylamino]benzoic acids, salts and derivatives of these of the present invention. These compounds may be utilized either as the free bases or in the form of a pharmaceutically acceptable salt with an organic or inorganic acid or base. The invention also contemplates a method for lowering serum lipids and for ameliorating atherosclerosis in mammals by the administration of said acids and derivatives.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an inbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscle and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of this invention are new and novel 4-mono[(cycloalkyl or cycloalkenyl substituted)amino, alkylamino or alkenylamino]benzoic acids, salts and derivatives of Formula I (including Formulas IA to IE) which have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These substances also provide the oral administration required of hypolipidemic agents, which patients usually take for many years. The novel compounds of this invention are adequately absorbed from the gastrointestinal tract. The 4-(monoalkylamino)benzoic acids and esters were disclosed in U.S. Pat. No. 3,868,416.

We have now found that the compounds of the present invention can safely and effectively lower both serum sterols and triglycerides in warm-blooded mammals. Such actions on serum-lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The novel compounds of the present invention are, in general, white crystalline solids having characteristic melting points and absorption spectra. They are soluble in organic solvents such as lower alkanol, chloroform, benzene, dimethylformamide, and the like but are generally not very soluble in water. The novel compounds of the present invention, which are organic bases, may be converted to their non-toxic acid-addition or cationic salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, ascorbic, and the like. The novel compounds of the present invention in their acidic forms or which contain acidic substituents are converted to their non-toxic organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

The cycloalkylamino, cycloalkenylamino, cycloalkylalkylamino, cycloalkyl-alkenylamino, cycloalkenylalkylamino, cycloalkyl-cycloalkylamino benzoic acids of this invention are prepared by reaction of loweralkyl p-aminobenzoates with suitable alkylating agents, such as cycloalkyl, cycloalkenyl, cycloalkyl-alkyl, cycloalkyl-alkenyl, cycloalkenyl-alkyl and cycloalkyl-cycloalkyl halides, sulfates, tosylates, mesylates or trifluoromethylsulfonates, with or without a solvent at 50°-150° C. Suitable solvents are lower alkanols, chloroform, N,N-dimethylformamide, N-N,-dimethylacetamide, diglyme, dimethylsulfoxide, acetonitrile, toluene, benzene, hexamethylphosphoramide and like solvents.

The reaction may be carried out with 2 equivalents of the alkyl aminobenzoate or with one equivalent of base, such as an unreactive organic base such as diisopropylethylamine or an alkali carbonate or bicarbonate, or with a catalytic amount of copper powder when an appropriate halide is used as the alkylating agent. The resulting benzoate esters are readily hydrolyzed to the acids in aqueous ethanolic alkali at 25°-100° C. for 1 to 24 hours.

The loweralkyl N-acetyl-4-(substituted amino)benzoates are prepared by reaction of a loweralkyl 4-(acetylamino)benzoate with an appropriate alkylating agent in the presence of an equivalent of sodium hydride in an inert solvent such as N,N-dimethylformamide, N,N-dimethylacetamide or diglyme at 50°-150° C. The N-acetyl benzoate esters are readily hydrolyzed and deacetylated to the acids in boiling aqueous ethanolic dilute alkali or acid.

Alternative methods of preparation are by reductive alkylation of a 4-aminobenzoic ester or amide which may also be generated in situ by reduction of 4-amino precursors such as a 4-nitro group and the like, or by a borohydride reduction of the chloroimide formed with phosphorus oxychloride from a 4-(acylamino)benzoate ester. For example, a cycloalkyl aldehyde or ketone plus 4-aminobenzoyl piperidide are reduced under 1–10 atmospheres of hydrogen using a metal catalyst, forming the 4-(cycloalkyl-alkylamino)benzoyl piperidide.

Two types of substitution reactions also yield the compounds of the present invention, namely, reaction of esters or amides of 3,4-didehydrobenzoic acid with an appropriate amine (or its alkali metal salt) and amination of 4-fluorobenzoate esters or amides. The former type of reaction in which the 3,4-didehydrobenzoic acid derivative is generated in situ, is carried out by treating a 4-halo compound such as 4-bromobenzoyl piperidide with the lithium, potassium or sodium salt of an amine (in excess) such as cyclohexylmethylamine in diethyl ether or other aprotic solvent. The latter type comprises reacting 2-cyclopentylethylamine or the like with 4-fluorobenzoyl piperidide at elevated temperature.

The novel compounds of the present invention where z is other than COOH may be readily prepared by treating an acid halide, mixed acid anhydride, or activated ester or amide of a compound of Formula I wherein Z is COOH with an appopriate a hydroxy compound, amine, or salt of a carboxamide or sulfonamide. These reactions are preferably carried out in an inert solvent at a temperature of 5°–125° C. for a period of time of from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdered sodium carbonate, and the like. The acid halide and anhydride starting materials may be obtained from the corresponding 4-(substituted amino)benzoic acids by methods which are well-known in the art or described herein. However, a protecting group on the arylamino nitrogen is used for best results. The simplest protecting group is provided by protonation of the amine to give an anilinium salt prior to or during formation of the acylating agent. Acylation of this amino group by carefully selected acyl groups such as carbobenzyloxy, carbo-t-butoxy, and trifluoroacetyl provides protection of this group from self-acylation during amide or ester formation. These protecting groups are then removed by catalytic hydrogenation, mild acid treatment and mild alkali treatment, respectively.

Activated esters or amides, which are used to synthesize the esters of the present invention, are carboxymethyl, 4-nitrophenyl, N-oxysuccinimide, 1-imidazolyl and the like. In certain cases, treatment of acids or ordinary esters such as methyl or ethyl with an excess of an appropriate hydroxy-containing substrate in the presence of a Lewis or mineral acid such as boron trifluoride, sulfuric acid, or hydrochloric acid is sufficient to convert the 4-(substituted amino)benzoic esters or acids to the appropriate esters.

With certain kinds of substrates for ester formation, it is necessary to form the alkali metal or strong organic base salts of the 4-(substituted amino)benzoic acids in order to react them with 2,3-dihydroxypropyl iodide, ethyl chloroacetate and the like. Other esters are prepared from the acids themselves by reaction with diazoalkanes, ethyl diazoacetate or the like.

The 4-(substituted amino)benzoic acids and derivatives are prepared by de-acylation of the corresponding 4-(N-trifluoroacetyl N-substituted amino)benzoic ester or amide by reacting with an alkali hydroxide such as sodium or potassium hydroxide in a lower alkanol, water or an aqueous lower alkanol at 5° C. to 50° C. Alternatively, these compounds may be prepared by de-acylation of the 4-(N-carbo-t-butoxy-N-substituted amino)benzamide and the like with mineral acids such as hydrochloric or hydrobromic acid, preferably in glacial acetic acid at 0° C. to 50° C. Also, they are prepared by removal of the carbobenzyloxy protecting group from the anilino nitrogen atom by means of mild catalytic hydrogenation or by treatment with a mineral acid such as hydrobromic acid in glacial acetic acid.

With certain kinds of substrates for amide formation, it is necessary to form the alkali metal or strong organic base salts of these substrates in order to react them with the various aforementioned acylating forms of the 4-(substituted amino)benzoic acids. The aminoalkanecarboxylic and aminoalkanesulfonic acids are zwitterionic and must be converted to their cationic salts, suitably in situ. They may also be used in the form of their esters and then hydrolyzed after amide formation. Certain substrates, which are neutral like the carboxamides or slightly acidic like the alkane or arene sulfonamides, are converted to reactive sodium salts by reaction with sodium hydride or other basic reagents.

Alternatively, the free acids may be prepared by hydrolysis of the corresponding nitriles or various amides, imidates or oxazolines. The carboxylic acid moiety may also be generated by oxidation of the corresponding aldehydes, acetophenones, benzyl alcohols, or alkylbenzenes, most often with the use of an amine-protecting group such as trifluoroacetyl or t-butyloxycarbonyl.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the 4-(substituted amino)benzoic acid, ester or amide with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon double bond of cinnamaldehyde itself.

The imidates of the present invention are preferably prepared either by addition of hydroxy compounds to the corresponding nitriles or by alkylation of the corresponding amides, suitably bearing a protecting group on the aminobenzoyl nitrogen atom in many cases. The addition of alcohols and other hydroxy compounds is carried out under acid catalysis without additional solvent, if possible. Alkylation of the protonated substituted aminobenzamide may be carried out or the aforementioned aminobenzoyl protecting groups can be employed. In some cases, simultaneous O-alkylation of the amide and N-alkylation of the aminobenzoyl moiety can be used to obtain a desired imidate. Intramolecular formation of imidates results from 2-haloethyl and 3-halopropyl amides as well as from 2-hydroxyethyl and 3-hydroxypropyl amides when treated with a condensing agent.

In certain cases, the unsaturation is introduced at a late stage of the preparation of the 4-(cycloalkyl unsaturated-alkylamino)benzoic acid derivatives. For example, an alkyl 4-cycloalkylhaloalkylamino)benzoate is dehydrohalogenated to the corresponding olefinic compound.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypochlolesteremic and antiatherosclerotic effect than the aforementioned adjuvants and medicaments. It is not known how these novel compounds operate in the blood serum and no theory of why these compounds so operate is advanced. It is not intended that the these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 to 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage-unit. For instance, tablets, pills, or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1

Preparation of p-[(cyclohexylmethyl)amino]benzoic acid

A solution of 6 g. of cyclohexylmethyl bromide and 11.19 g. of ethyl p-aminobenzoate in 30 ml. of hexamethylphosphoramide is heated in an oil bath for 20 hours. The solution is poured into ice-cold water and extracted several times with diethyl ether. The combined ether extracts are washed with water, dried with anhydrous magnesium sulfate, and evaporated to dryness under reduced pressure to furnish ethyl p-cyclohexylmethylaminobenzoate as an oil.

The oil is dissolved in 250 ml. of ethanol:water (9:1) containing 9 g. of potassium hydroxide and the resulting solution is stirred at the reflux temperature for 3 hours. After chilling, the mixture is acidified with concentrated hydrochloric acid, diluted with water, and extracted twice with methylene chloride. The combined extracts are washed with water, dried with anhydrous magnesium sulfate, and evaporated to dryness under reduced pressure to furnish p-[(cyclohexylmethyl)amino]-benzoic acid.

EXAMPLES 2–108

Treatment of the indicated halide starting materia set forth in Table I below with ethyl p-aminobenzoate followed by saponification according to Example 1 is productive of the corresponding p-[substituted amino]-benzoic acids listed in Table I.

TABLE I

| Example | Starting material | Product |
| --- | --- | --- |
| 2 | 1-iodomethyl-2-methyl cyclopentane, Chem Abst. 67, 90421y | p-[(2-methylcyclopentyl)methylamino]benzoic acid |
| 3 | α-bromomethyl cyclopen- | p-[(cyclopentyl)methyl- |

TABLE I-continued

| Example | Starting material | Product |
|---|---|---|
| | tane Chem. Abst. 66, 18472c | amino]benzoic acid |
| 4 | 1-bromomethyl-4-methyl-cyclohexane Chem. Abst. 70, 2934b | p-[(4-methylcyclo-hexyl)methylamino]-benzoic acid |
| 5 | 1-chloromethyl-2-methyl-cyclohexane Chem. Abst. 68, 88671h | p-[(2-methylcyclo-hexyl)methylamino]ben-zoic acid |
| 6 | 1-(1,2-dimethylcyclo-hexyl)-2-chloropropane Chem. Abst. 73, 14272j | p-[1-(1,2-dimethyl-cyclohexyl)-2-propyl-amino]benzoic acid |
| 7 | 1-(1,3-dimethylcyclo-hexyl)-2-chloropropane Chem. Abst. 73, 14272j | p-[1-(1,3-dimethyl-cyclohexyl)-2-propyl-amino]benzoic acid |
| 8 | 1-(1,4-dimethylcyclo-hexyl)-2-chloropropane Chem Abst. 73, 14272j | p-[1-(1,4-dimethyl-cyclohexyl)-2-propyl-amino]benzoic acid |
| 9 | α-bromomethylcyclo-heptane Chem. Abst. 51, 1049e | p-(cycloheptylmethyl-amino)benzoic acid |
| 10 | α-bromomethylcyclo-octane Chem. Abst. 68, 104595t | p-(cyclooctylmethyl-amino)benzoic acid |
| 11 | α-chloroethylcyclo-pentane Chem. Abst. 72, 110862b | p-(1-cyclopentylethyl-amino)benzoic acid |
| 12 | 1-bromo-2-cyclo-pentylbutane | p-(2-cyclopentylbutyl-amino)benzoic acid |
| 13 | 1-bromo-2-cyclopentyl-hexane Ref. A | p-(2-cyclopentylhexyl-amino)benzoic acid |
| 14 | 2-chloroethylcyclo-hexane Chem. Abst. 68, 86671h | p-(2-cyclohexylethyl-amino)benzoic acid |
| 15 | 1-(2-bromoethyl)-1-ethylcyclohexane Chem. Abst. 70, 57233c | p-[2-(1-ethylcyclo-hexyl)ethylamino] benzoic acid |
| 16 | 1-bromo-2-(3-methyl-cyclohexyl)butane Ref. A | p-[2-(3-methylcyclo-hexyl)butylamino] benzoic acid |
| 17 | 1-bromo-2-cyclohexyl-pentane Ref. A | p-[(2-cyclohexyl)pen-tylamino]benzoic acid |
| 18 | 1-bromo-2-cyclohexyl-butane Ref. A | p-[(2-cyclohexyl)butyl-amino]benzoic acid |
| 19 | 1-bromo-2-cyclohexyl-propane Ref. A | p-[(2-cyclohexyl)propyl-amino]benzoic acid |
| 20 | 1-(2-chloroethyl)-2,3-dimethylcyclohexane Chem. Abst. 69, 56053n | p-[2-(2,3-dimethylcyclo-hexyl)ethylamino]benzoic acid |
| 21 | 1-(2-chloroethyl)-3,5-dimethylcyclohexane Chem. Abst. 69, 56053n | p-[2-(3,5-dimethylcyclo-hexyl)ethylamino]benzoic acid |
| 22 | 2-(2-chloroethyl)-1,4-dimethylcyclohexane Chem. Abst. 69, 56053n | p-[2-(2,5-dimethylcyclo-hexyl)ethylamino]benzoic acid |
| 23 | 1-(2-chloroethyl)-2-ethylcyclohexane Chem. Abst. 69, 56053n | p-[2-(2-ethylcyclo-hexyl)ethylamino]benzoic acid |
| 24 | 1-(2-chloropropyl)-3-methylcyclohexane Chem. Abst. 67, 53405a | p-[1-(3-methylcyclo-hexyl)-2-propylamino] benzoic acid |
| 25 | 1-(2-bromoethyl)-1-methylcyclohexane Chem. Abst. 72, 132133s | p-[2-(1-methylcyclo-hexyl)ethylamino]benzoic acid |
| 26 | 1-(2-chloroethyl)-2-methylcyclohexane Chem. Abst. 69, 56053n | p-[2-(2-methylcyclo-hexyl)ethylamino]benzoic acid |
| 27 | 1-(2-chloroethyl)-3-methylcyclohexane Chem. Abst. 69, 56035n | p-[2-(3-methylcyclo-hexyl)ethylamino]benzoic acid |
| 28 | 1-(2-chloroethyl)-4-methylcyclohexane Chem. Abst. 69, 56053n | p-[2-(4-methylcyclo-hexyl)ethylamino]benzoic acid |
| 29 | 2-bromomethylcyclo-heptane Ref. A | p-(cycloheptylmethyl-amino)benzoic acid |
| 30 | 3-bromopropylcyclo-butane Ref. A | p-(3-cyclobutyl)propyl-aminobenzoic acid |
| 31 | 3-bromopropylcyclo-pentane Chem. Abst. 75, 15138f | p-(3-cyclopentyl)propyl-aminobenzoic acid |

TABLE I-continued

| Example | Starting material | Product |
|---|---|---|
| 32 | 3-bromopropylcyclohexane Ref. A | p-(3-cyclohexyl)propylaminobenzoic acid |
| 33 | 1-(3-chloropropyl)-3-ethylcyclohexane Chem. Abst. 68, 12589w | p-[3-(3-ethylcyclohexyl)propylamino]benzoic acid |
| 34 | 1-(3-bromopropyl)-3-methylcyclohexane Chem. Abst. 75, 151387f | p-[3-(3-methylcyclohexyl)propylamino]benzoic acid |
| 35 | 1-(3-bromopropyl)-4-methylcyclohexane Chem. Abst. 75, 151387f | p-[3-(4-methylcyclohexyl)propylamino]benzoic acid |
| 36 | 1-bromo-3-cyclohexylpentane Ref. A | p-[(3-cyclohexyl)pentylamino]benzoic acid |
| 37 | (2-bromomethyl)butylcyclohexane Ref. A | p-[(3-cyclohexyl-2-ethyl)propylamino]benzoic acid |
| 38 | 1-[1-bromo-2-methyl-3-(3-ethylcyclohexyl)]propane Chem. Abst. 68, 12529w | p-[3-(3-ethylcyclohexyl)-2-methyl]propylaminobenzoic acid |
| 39 | 4-bromobutylcyclopentane Chem. Abst. 69, 18646z | p-(4-cyclopentyl)butylaminobenzoic acid |
| 40 | 4-chlorobutylcyclohexane Ref. A | p-(4-cyclohexyl)butylaminobenzoic acid |
| 41 | 5-bromo-2-cyclohexylpentane Ref. A | p-(4-cyclohexyl)pentylaminobenzoic acid |
| 42 | 1-bromo-4-cyclohexylhexane Ref. A Chem. Abst. 70, P87143r | p-(4-cyclohexyl)hexylaminobenzoic acid |
| 43 | 1-bromo-4-cyclohexyl-2-ethylbutane Ref. A | p-(4-cyclohexyl-2-ethyl)butylaminobenzoic acid |
| 44 | 1-bromo-4-(3-methylcyclohexyl)butane Ref. A | p-[4-(3-methylcyclohexyl)butylamino]benzoic acid |
| 45 | 1-chloro-4-(4-methylcyclohexyl)butane Ref. A | p-[4-(4-methylcyclohexyl)butylamino]benzoic acid |
| 46 | 1-chloro-4-(4-ethylcyclohexyl)butane Ref. A | p-[4-(4-ethylcyclohexyl)butylamino]benzoic acid |
| 47 | 1-(4-chlorobutyl)-2,3-dimethylcyclohexane Chem. Abst. 70, P87143r; Ref. A | p-[4-(2,3-dimethylcyclohexyl)butylamino]benzoic acid |
| 48 | 1-(4-chlorobutyl)-2,5-dimethylcyclohexane Ref. A | p-[4-(2,5-dimethylcyclohexyl)butylamino]benzoic acid |
| 49 | 1-(4-chlorobutyl)-4-methoxycyclohexane Ref. A | p-[4-(4-methoxycyclohexyl)butylamino]benzoic acid |
| 50 | 1-(4-bromobutyl)-2-methoxycyclohexane Ref. A | p-[4-(2-methoxycyclohexyl)butylaminobenzoic acid |
| 51 | 4-bromobutyl)cycloheptane Ref. A | p-(4-cycloheptyl)butylaminobenzoic acid |
| 52 | 1-(4-chlorobutyl)-4-cyclohexylcyclohexane Ref. A | p-[4-(4-cyclohexyl)cyclohexyl]butylamino benzoic acid |
| 53 | 2-(4-chlorobutyl)decahydronaphthylene Ref. A | p-[4-(2-decahydronaphthyl]butylamino benzoic acid |
| 54 | 4-bromobutylcycloheptane Chem. Abst. 70, P87143r | p-(4-cycloheptyl)butylamino benzoic acid |
| 55 | 4-chloropentylcyclopropane Chem. Abst. 69, 105732t, 74, 31488x | p-[5-(cyclopropyl)-2-pentylamino]benzoic acid |
| 56 | 1-bromo-5-cyclobutylpentane Chem. Abst. 70, P87143r; Ref. A | p-[5-(cyclobutyl)pentylamino]benzoic acid |
| 57 | 1-chloro-5-cyclopentylpentane Chem. Abst. 70, P8143r; Ref. A | p-[5-(cyclopentyl)pentylamino]benzoic acid |
| 58 | 5-bromopentylcyclohexane | p-[5-(cyclohexyl)pentyl- |

TABLE I-continued

| Example | Starting material | Product |
|---|---|---|
| | Chem. Abst. 55, 21016e | aminobenzoic acid |
| 59 | 5-chloropentylcycloheptane Chem. Abst. 70, P87143r; Ref. A | p-[5-(cyclopentyl)pentyl-amino]benzoic acid |
| 60 | 6-chlorohexylcyclopentane Ref. A | p-[6-(cyclopentyl)hexyl-amino]benzoic acid |
| 61 | 6-chlorohexylcycloheptane Chem. Abst 70, P87143r | p-[6-(cycloheptyl)hexyl-amino]benzoic acid |
| 62 | 1-chloro-7-cyclopentyl-heptane Chem. Abst. 75, P141605n | p-[7-(cyclopentyl)heptyl-amino]benzoic acid |
| 63 | 8-chlorooctylcyclopentane Ref. A; Chem. Abst. 70, 87143r | p-[8-(cyclopentyl)octyl-amino]benzoic acid |
| 64 | 8-bromooctylcyclohexane | p-[8-(cyclohexyl)octyl-amino]benzoic acid |
| 65 | 1-bromo-8-(3,3,5-trimethyl-cyclohexyl)octane Chem. Abst. 75, P20026q | p-[8-(3,3,5-trimethyl-cyclohexyl)octylamino]-benzoic acid |
| 66 | 9-bromononylcyclopentane Ref. A; Chem. Abst. 70, P87143r | p-[9-(cyclopentyl)nonyl-amino]benzoic acid |
| 67 | 13-bromotridecylcyclopentane | p-[13-(cyclopentyl)tri-decylamino]benzoic acid |
| 68 | 1-(2-chlorocyclopropyl)-pentane Chem. Abst. 75, 49270a | p-[2-pentyl)cyclopropyl-amino]benzoic acid |
| 69 | 1-bromocyclopropylpentane Chem. Abst. 75, 76195n | p-[1-pentyl)cyclopropyl-amino]benzoic acid |
| 70 | 1-(2-bromocyclopropyl)butane Chem. Abst. 74, 124924b | p-[2-butylcyclopropyl)-amino]benzoic acid |
| 71 | bromocyclopentane Ref. A | p-cyclopentylamino-benzoic acid |
| 72 | 1-chloro-1-propylcyclo-pentane Chem. Abst. 52, 8978a | p-(1-propylcyclopentyl-amino)benzoic acid |
| 73 | 4-bromo-1,1-dimethylcyclo-hexane Chem. Abst. 71, 11242c | p-(4,4-dimethylcyclohexyl-amino)benzoic acid |
| 74 | 1-chloro-4-propylcyclo-hexane Chem. Abst. 68, 86671h; 75, 128994t | p-(4-propylcyclohexyl-amino)benzoic acid |
| 75 | 2-chloro-1-methylethyl-cyclohexane Cnem. Abst. 70, P87143r; 75, 128994t | p-[2(1-methylethyl)cyclo-hexylamino]benzoic acid |
| 76 | 4-(t-butyl)-1-chloro-1-methylcyclohexane Chem. Abst. 68, 113898w | p-[4-(t-butyl)-1-methyl-cyclohexylamino]benzoic acid |
| 77 | bromocycloheptane Chem. Abst. 51, 9505e; 67. 9986s | p-cycloheptylamino-benzoic acid |
| 78 | bromocyclooctane Chem. Abst. 51, 1049e; 67, 107842n | p-cycloheptylamino-benzoic acid |
| 79 | bromocyclononane Chem. Abst. 54, 4153f; 69, 2306v | p-cyclononylamino-benzoic acid |
| 80 | bromocyclodecane Chem. Abst. 67, 58849h; 69, 2306c | p-cyclodecylamino-benzoic acid |
| 81 | bromocycloundecane Chem. Abst. 69, 2306c | p-cycloundecylamino-benzoic acid |
| 82 | bromocyclododecane Chem. Abst. 54, 4153f; 69, 2306c | p-cyclododecylamino-benzoic acid |
| 83 | bromocyclotridecane Chem. Abst. 69, 2306c | p-cyclotridecylamino-benzoic acid |
| 84 | bromocyclotetradecane Chem. Abst. 54, 4153f; 54, 16141i | p-cyclotetradecylamino-benzoic acid |
| 85 | bromocyclopentadecane Chem. Abst. 72, P100160g | p-cyclopentadecylamino-benzoic acid |
| 86 | bromocyclohexadecane Chem. Abst. 69, 2306c | p-cyclohexadecylamino-benzoic acid |
| 87 | 3-bromobicyclopentyl Chem. Abst. 31, 7405[3]; 35, 2864[5] | p-(3-cyclopentyl)cyclo-pentylamino)benzoic acid |
| 88 | (3-bromocyclopentyl)cyclohexane Chem. Abst 31, 7405[4] | p-(3-cyclohexylcyclopentyl-amino)benzoic acid |
| 89 | 3-bromo-3'-ethylbicyclo-pentyl Chem. | p-[3-(3-ethylcyclopentyl)-cyclopentylamino]benzoic |

TABLE I-continued

| Example | Starting material | Product |
|---|---|---|
| | Abst. 36, 48089 | acid |
| 90 | 2-bromo-1-cyclopentyl-cyclopentane Chem. Abst. 51, 5712f | p-[2-(cyclopentyl)cyclo-pentylamino]benzoic acid |
| 91 | 1-chlorobicyclohexyl Chem. Abst. 30, 3807[1] | p-[1-(cyclohexyl)cyclohexyl-amino]benzoic acid |
| 92 | 1-chorobicyclopentyl Chem. Abst. 45, 6163b | p-[1-(cyclopentyl)cyclo-pentylamino]benzoic acid |
| 93 | 2-iodomethyldecahydro-naphthalene Chem. Abst. 41, 116b | p-[(2-decahydronaphthyl)-methylamino]benzoic acid |
| 94 | 2-(2-iodoethyl)deca-hydronaphthalene Chem. Abst. 41, 116d | p-[2-(2-decahydronaphthyl)-ethylamino]benzoic acid |
| 95 | 1-(4-bromobutyl)deca-hydronaphthalene Chem. Abst. 45, P175d | p-[4-(1-decahydronaphthyl)-butylamino]benzoic acid |
| 96 | 1-bromo-1,1-dicyclo-pentylethane Chem. Abst. 31, 5759[2] | p-[(1,1-dicyclopentyl)ethyl-amino]benzoic acid |
| 97 | 1-bromo-4-α-methyldeca-hydronaphthalene Chem. Abst. 53, 3265f | p-[1-(4α-methyldecahydro-naphthyl)amino]benzoic acid |
| 98 | 2-(bromomethyl)-1,3,3-trimethylcyclohexane Chem. Abst. 28, 2343[8] | p-[(1,3,3-trimethylcyclo-hexyl)methylamino]benzoic acid |
| 99 | 6-(3-bromobutyl)-1,5,5-trimethylcyclohexene Chem. Abst. 66, 2658g | p-[4-(2,6,6-trimethyl-2-cyclohexenyl)-2-butylamino]-benzoic acid |
| 100 | 4-(3-chloropropyl)-cyclohexene Ref. A | p-[3-(3-cyclohexenyl)-propylamino]benzoic acid |
| 101 | 3-(4-chlorobutyl)-cyclopentene Ref. A | p-[4-(3-cyclopentenyl)-butylamino]benzoic acid |
| 102 | 1-(4-bromobutyl)cyclo-hexene Chem. Abst. 69, 76727n | p-[4-(1-cyclohexenyl)butyl-amino]benzoic acid |
| 103 | 1-(5-bromopentyl)-cyclopentene Chem. Abst. 55, 27129g | p-[5-(1-cyclopentenyl)-pentylamino]benzoic acid |
| 104 | 3-(11-chloroundecyl)-cyclopentene Chem. Abst. 37, 3060f | p-[11-(3-cyclopentenyl)-undecylamino]benzoic acid |
| 105 | 1-(13-chlorotridecyl-cyclopentene Chem. Abst. 37, 5031b | p-[13-(1-cyclopentyl)tri-decylamino]benzoic acid |
| 106 | 3-(13-chlorotridecyl)-cyclopentene Chem. Abst. 51, 7652a | p-[1-(cyclohexyl)cyclohexyl-amino]benzoic acid |
| 107 | 2-(4-chlorobutyl)deca-hydronaphthalene Chem. Abst. 70, P87143r | p-[4-(2-decahydronaphthyl)-butylamino]benzoic acid |
| 108 | 4-bromo-1-(cyclohexyl)-cyclohexane Chem. Abst. 69, 103618m | p-[4-(cyclohexyl)cyclo-hexylbutylamino]benzoic acid |

Ref. A = R. D. Westland, et al., J. Med Chem., 11, 1190 (1968).

EXAMPLE 109

Preparation of p-[2-(cyclopentyl)ethylamino]benzoic acid

To a solution of 5 g. of 2-cyclopentylethanol and 9.15 ml. of triethylamine in 75 ml. of dry methylene chloride (cooled in an ice-salt bath) in an argon atmosphere, is added a solution of 8.39 g. of methanesulfonic anhydride in 50 ml. of methylene chloride dropwise over a period of 15 minutes. After stirring at −10° C. for 50 minutes the solution is washed successively with 30 ml. portions of ice-cold water, 5% hydrochloric acid, saturated sodium bicarbonate solution, saturated sodium chloride solution, dried with anhydrous magnesium sulfate, and taken to dryness under reduced pressure to provide 8.4 g. (99%) of 2-cyclopentylethyl methanesulfonate.

A solution of 5 g. of 2-cyclopentylethyl methanesulfonate and 8.59 g. of ethyl p-aminobenzoate in 30 ml. of hexamethylphosphoramide is stirred at 110° C. under argon atmosphere for 18 hours. The cooled solution is diluted with 30 ml. of water and the resulting tan solid is collected by filtration. Recrystallization from ethanol-water furnishes ethyl p-[2-(cyclopentyl)ethyl-]aminobenzoate as off-white crystals.

A solution of 2 g. of ethyl p-[2-(cyclopentyl)ethylamino]benzoate in 50 ml. of ethanol:water (9:1) containing 2 g. of potassium hydroxide is stirred at the reflux temperature under argon atmosphere for 3 hours. The chilled solution is acidified with concentrated hydrochloric acid, diluted with 45 ml. of water, and filtered to furnish 1.52 g. of white crystals. Recrystallization from ethanol/hexane provided product as white crystals.

EXAMPLES 110–188

Treatment of the alcohols of Table II below with methanesulfonic anhydride to provide the corresponding mesylate, followed by treatment with ethyl p-aminobenzoate followed by saponification and acidification of the resulting substituted aminobenzoate by the procedure of Example 109 produces the indicated p-(substituted amino)benzoic acids shown in Table II.

TABLE II

| Example | Starting Material | Product |
|---|---|---|
| 110 | 2-isopropyl-5-methyl-enecyclopentanol Chem. Abst. 66, 38074c | p-(2-isopropyl-5-methylenecyclopentylamino)benzoic acid |
| 111 | 2-cyclohexen-1-ol Aldrich Chem. Co. | p-(cyclohex-2-enylamino)benzoic acid |
| 112 | 4-isopropyl-2-cyclohexen-1-ol Chem. Abst. 69, 99290d | p-(4-isopropylcyclohex-2-enylamino)benzoic acid |
| 113 | 2-isopropyl-3-cyclohexen-1-ol Chem. Abst. 75, 55380m | p-(2-isopropylcyclohex-3-enylamino)benzoic acid |
| 114 | 2-methyl-2-cycloocten-1-olopentane Chem. Abst. 69, 27127h | p-(2-(cyclopentyl)cyclopentylamino)benzoic acid |
| 115 | 2-cyclononen-1-ol Chem. Abst. 72, 30882t | p-(cyclonon-2-enylamino)benzoic acid |
| 116 | 3-cyclononen-1-ol Chem. Abst. 75, 13957j | p-(cyclonon-3-enylamino)benzoic acid |
| 117 | 2-methylenecyclodecanol Chem. Abst. 74, 75857w | p-(2-methylenecyclodecylamino)benzoic acid |
| 118 | E-3-cyclodecen-1-ol Chem. Abst. 73, 87173n | p-(E-cyclodec-3-enylamino)benzoic acid |
| 119 | Z-3-cyclodecen-1-ol Chem. Abst. 73, 87173n | p-(Z-cyclodec-3-enylamino)benzoic acid |
| 120 | 5-cyclodecen-1-ol Chem. Abst. 71, 60514w | p-(cyclodec-5-enylamino)benzoic acid |
| 121 | 4-ethyl-2-cyclododecen-1-ol Chem. Abst. 70, 114922c | p-(4-ethylcyclododec-2-enylamino)benzoic acid |
| 122 | 2-cyclotridecen-1-ol Chem. Abst. 70, 114922c | p-(cyclotridec-2-enylamino)benzoic acid |
| 123 | 8-cycloheptadecen-1-ol Chem. Abst. 66, 2658g | p-(cycloheptadec-8-enylamino)benzoic acid |
| 124 | 9-cycloheptadecen-1-ol Chem. Abst. 68, 49157z | p-(cycloheptadec-9-enylamino)benzoic acid |
| 125 | 2-cyclobutene-1-methanol Chem. Abst. 67, 32343p | p-[(cyclobut-2-enyl)methylamino]benzoic acid |
| 126 | 1-cyclobutene-1-methanol Chem. Abst. 70, 10736d | p-[1-(cyclobut-1-enyl)ethylamino]benzoic acid |
| 127 | 2-cyclopentene-1-methanol Chem. Abst. 71, 12650r | p-[(cyclopent-3-enyl)methylamino]benzoic acid |
| 128 | 3-cyclopentene-1-methanol Chem. Abst. 73, 65783j | p-(4-isopropylcyclohex-2-enylamino)benzoic acid |
| 129 | 1-cyclopentene-1-propanol Chem. Abst. 73, 66113c | p-(1-cyclopent-1-enyl)propylamino]benzoic acid |
| 130 | 1-cyclohexene-1-methanol Chem. Abst. 70, 10773p | p-[(cyclohex-1-enyl)methylamino]benzoic acid |
| 131 | 2-cyclohexene-1-ethanol, 30882t Chem. Abst. 69, 26424r | p-[(1-cyclohex-2-enyl)ethylamino]benzoic acid |
| 132 | 1-(3-cyclohexenyl)-1-propanol Chem. Abst. 67, 72634r | p-[(1-cyclohex-3-enyl)propylamino]benzoic acid |
| 133 | cis-5-ethyl-3-cyclohexene-1-methanol Chem. Abst. 69, 27575c | p-(cis-5-ethylcyclohex-3-enyl)methylaminobenzoic acid |
| 134 | trans-5-ethyl-3-cyclohexene-1-methanol Chem. Abst. 69, 27575c | p-(trans-5-ethylcyclohex-3-enyl)methylaminobenzoic acid |
| 135 | 1-cycloheptene-1-methanol Chem. Abst. 73, 14266k | p-(cyclohept-1-enylmethylamino)benzoic acid |
| 136 | 1-cycloheptene-1-ethanol Chem. Abst. 70, 37270j | p-[1-(cyclohept-1-enyl)ethylamino]benzoic acid |
| 137 | 2-cyclooctene-1-methanol Chem. Abst. 69, 36363b | p-(cyclooct-2-enylmethylamino)benzoic acid |
| 138 | 4-cyclooctene-1-methanol Chem. Abst. 66, 37492a | p-(cyclooct-4-enylmethylamino)benzoic acid |
| 139 | 1-cyclooctenylethanol Chem. Abst. 70, 37270j | p-(cyclooct-1-enylethylamino)benzoic acid |
| 140 | 2-(3-cyclopentenyl)butanol Chem. Abst. 72, 133044a | p-[2-ethyl-2-cyclopent-3-enylethylamino]benzoic acid |
| 141 | 2,3-dimethyl-2-(2-cyclopentenyl)propanol Chem. Abst. 70, 11818u | p-[2-(2,3-dimethylcyclopent-2-enyl)propylamino]benzoic acid |
| 142 | 4,6-dimethyl-3-cyclohexen-1-ethanol Chem. Abst. 74, 111623c | p-[2-(4,6-dimethylcyclohex-3-enyl)ethylamino]benzoic acid |
| 143 | α-methyl-1-cyclohexene-1-ethanol Chem. Abst. 74, 42909v | p-[1-methyl-2-(cyclohex-1-enyl)ethylamino]benzoic acid |
| 144 | 4-methyl-3-cyclohexene-1-ethanol Chem. Abst. 75, 19601s | p-[2-(4-methylcyclohex-3-enyl)ethylamino]benzoic acid |
| 145 | 1-cyclooctene-1-ethanol Chem. Abst. 70, 37270j | p-(2-cyclooct-1-enylethylamino)benzoic acid |
| 146 | 1-cyclononene-1-ethanol | p-(2-cyclonon-1-enylethylamino)benzoic acid |
| 147 | α,4-dimethyl-3-cyclohexene-1-propanol Chem. Abst. 68, 78427L | p-[1-methyl-3-(4-methylcyclohex-3-enyl)propylamino]benzoic acid |
| 148 | 1-cyclohexene-1-propanol Chem. Abst. 70, 87111d | p-(3-cyclohex-1-enylpropylamino)benzoic acid |
| 149 | 3-cyclohexene-1-propanol Chem. Abst. 69, 43158z | p-(3-cyclohex-3-enylpropylamino)benzoic acid |
| 150 | 3-cyclohexene-1-butanol Chem. Abst. 69, 49158z | p-(4-cyclohex-3-enylbutylamino)benzoic acid |
| 151 | α,α-dimethyl-2-cyclopentene-1-undecanol Chem. Abst. 72, 110860z | p-[(1,1-dimethyl-11-cyclopent-2-enyl)undecylamino]benzoic acid |
| 152 | 4-isopropylidene-2,2-dimethylcyclobutanol Chem. Abst. 73, 24996n | p-(2,2-dimethyl-4-isopropylidenecyclobutylamino)benzoic acid |
| 153 | 2-cyclopenten-1-ol Chem. Abst. 68, 39177s | p-(cyclopent-2-enylamino)benzoic acid |
| 154 | 3-cyclopenten-1-ol Chem. Abst. 66, 11504r | p-(cyclopent-3-enylamino)benzoic acid |
| 155 | 3-cyclohexen-1-ol Chem. Abst. 69, 26837c | p-(cyclohex-3-enylamino)benzoic acid |
| 156 | 2,2-dimethyl-6-methylenecyclohexanol | p-(2,2-dimethyl-6-enylcyclohexylamino)benzoic acid |
| 157 | 2-methylenecycloheptanol Chem. Abst. 69, 27127h | p-(2-methylenecycloheptylamino)benzoic acid |
| 158 | 2-methyl-2-cyclohepten-1-ol Chem. Abst. 69, 27127h | p-(2-methylcyclohept-2-enylamino)benzoic acid |
| 159 | 2-methyl-6-methylenecycloheptanol Chem. Abst. 67, 11600e | p-(2-methyl-6-methylenylcycloheptylamino)benzoic acid |
| 160 | 3,7-dimethyl-3-cyclohepten-1-ol Chem. Abst. 67, 11600e | p-(3,7-dimethylcyclohept-3-enylamino)benzoic acid |
| 161 | 4-cycloocten-1-ol Chem. Abst. 70, 28287t | p-(cyclooct-4-enylamino)benzoic acid |
| 162 | 3-cycloocten-1-ol Chem. Abst. 66, 104593z | p-(cyclooct-3-enylamino)benzoic acid |
| 163 | 2-cycloocten-1-ol Chem. Abst. 68, 39177s | p-(cyclooct-2-enylamino)benzoic acid |
| 164 | 4-methylenecyclooctanol Chem. Abst. 70, 28445t | p-(4-methylenecyclooctylamino)benzoic acid |
| 165 | α-methyl-5-methylene- | p-[1-(5-methylenecyclooctyl)- |

TABLE II-continued

| Example | Starting Material | Product |
|---|---|---|
| | cyclooctanemethanol Chem. Abst. 68, 10459t | ethylamino]benzoic acid |
| 166 | 5-methylenecyclo-octanemethanol Chem. Abst. 66, 37492a | p-(5-methylenecyclooctyl-methylamino)benzoic acid |
| 167 | 1,3-dimethyl-2-methyl-enecyclopentane-methanol Chem. Abst. 73, 24996n | p-[(1,3-dimethyl-2-methylene-cyclopentyl)methylamino benzoic acid |
| 168 | E-4-cyclopropyl-3-buten-2-ol Chem. Abst. 70, 3413t | p-[E-2-(4-cyclopropyl)but-3-enylamino]benzoic acid |
| 169 | Z-4-cyclopropyl-3-buten-2-ol Chem. Abst. 70, 3413t | p-[Z-2-(4-cyclopropyl)but-3-enylamino]benzoic acid |
| 170 | α-methylenecyclo-hexaneethanol Chem. Abst. 66, 45950p | p-[(1-methylene-2-cyclo-hexyl)ethylamino]benzoic acid |
| 171 | β-methylenecyclo-hexaneethanol Chem. Abst. 75, 139951c | p-[(2-methylene-2-cyclo-hexyl)ethylamino)benzoic acid |
| 172 | E-2-(3,3-dimethylcyclo-hexylidenyl)ethanol Chem. Abst. 75, 110431x | p-[E-2-(3,3-dimethylcyclo-hexylidenyl)ethyl]amino benzoic acid |
| 173 | Z-2-(3,3-dimethylcyclo-hexylidenyl)ethanol Chem. Abst. 75, 110431x | p-[Z-2-(3,3-dimethylcyclo-hexylidenylethylamino]-benzoic acid |
| 174 | E-4-cyclopentyl-2-buten-1-ol Chem. Abst. 75, 48349w | p-[4-cyclopentylbut-2-enyl-amino)benzoic acid |
| 175 | E-4-cyclohexyl-2-buten-1-ol Chem. Abst. 75, 48349w | p-(E-4-cyclohexylbut-2-en-ylamino)benzoic acid |
| 176 | 2-vinylcyclopentane-ethanol Chem. Abst. 66, 10477q | p-[2-(2-vinylcyclopentyl)-ethylamino]benzoic acid |
| 177 | 3-isopropyl-1-methyl-cyclopentanemethanol Chem. Abst. 66, 38061w | p-[(3-isopropyl-2-methyl-cyclopentyl)methylamino]-benzoic acid |
| 178 | 1-allyl-2-methylcyclo-hexanol Chem. Abst. 71, 29919h | p-(1-allyl-2-methylcyclo-hexylamino)benzoic acid |
| 179 | 2-isopropenylcyclo-hexanol Chem. Abst. 72, 12663t | p-(2-isopropenylcyclo-hexylamino)benzoic acid |
| 180 | 1-(isopropenylcyclo-hexanol Chem. Abst. 75, 139951c | p-(1-isopropenylcyclohexyl-amino)benzoic acid |
| 181 | 2-allylcyclohexanol Chem. Abst. 70, 96517t | p-(2-allylcyclohexylamino)-benzoic acid |
| 182 | 3-allylcyclohexanol Chem. Abst. 69, 86453j | p-(3-allylcyclohexylamino)-benzoic acid |
| 183 | 1-allylcyclohexanol Chem. Abst. 66, 374866 | p-(1-allylcyclohexylamino)-benzoic acid |
| 186 | 1-(3-butenyl)-2-methyl-cycloheptanol Chem. Abst. 69, 106892g | p-[1-(3-butenyl)-2-methyl-cycloheptylamino]benzoic acid |
| 187 | 1-allylcyclododecanol Chem. Abst. 68, 95381r | p-(1-allylcyclododecyl-amino)benzoic acid |
| 188 | 2-butyl-2-cyclopenten-1-ol Chem. Abst. 71, 38404p | p-(2-butylcyclopent-2-en-ylamino)benzoic acid |

EXAMPLE 189

Preparation of methyl esters

Treatment of a methylene chloride solution of the 4-(substituted amino)benzoic acids of Examples 1-188 with a solution of diazomethane in ethanol until a yellow color persists (excess) followed by concentration and purification, if necessary, is productive of the corresponding methyl 4-(substitutedamino)benzoate.

EXAMPLE 190

Preparation of hexyl esters

Treatment of a methylene chloride solution of the 4-(substituted amino)benzoic acids of Examples 1-88 with excess diazohexane in diethyl ether, followed by concentration and purification, is productive of the corresponding hexyl 4-(substituted amino)benzoate.

EXAMPLE 191

Preparation of p-cyclohexylaminobenzhydroxamic acid

To a suspension of p-cyclohexylaminobenzoic acid (44 g.) in glymer (350 ml.) and pyridine (70 ml.) at 0° C. is added trifluoroacetic anhydride (67 ml., 100 g.) at such a rate as to maintain the temperature at 20°-30° C. The resulting solution is stirred at 10°-15° C. for 2 hours, then diluted with ether (400 ml.), cooled in an ice-bath and ice (100 gm.) is added. The mixture is stirred vigorously at ambient temperature for 1 hour. The aqueous layer is extracted with ether and the combined ether extracts are washed with water, brine, dried over sodium sulfate and concentrated in vacuo to provide p-[N-trifluoroacetyl-N-cyclohexylamino]benzoic acid as an oil that solidifies upon standing.

The N-trifluoroacetyl derivative (57 g.) is dissolved in thionyl chloride (300 ml.) and refluxed for 3 hours. After cooling, the mixture is diluted with toluene and concentrated in vacuo. The residue is diluted again with toluene and filtered. The toluene is concentrated in vacuo to provide N-trifluoroacetyl-p-cyclohexylaminobenzoylchloride as an oil.

To a stirred solution of hydroxylamine hydrochloride (16 g.) in pyridine (75 ml.) and dichloromethane (35 ml.) is added dropwise the previously prepared benzoyl chloride derivative (11.6 g.) in dichloromethane (20 ml.). After 1 hour, the mixture is diluted with water and extracted with ether. The combined organic extract is washed with 5% hydrochloric acid until the aqueous wash remains acidic. The ether extract is then washed with water, brine, dried with sodium sulfate and concentrated in vacuo to afford N-trifluoroacetyl-p-cyclohexylaminobenzhydroxamic acid as an oil.

This oil (0.9 g.) is dissolved in ethanol (20 ml.) and 1 N sodium hydroxide (2 ml.) is added. After 12 hours the solution is chilled and filtered to provide a white solid that is washed with ether.

The white solid is recrystallized from hot ethanol to provide p-(cyclohexylamino)benzhydroxamic acid.

EXAMPLE 192

Preparation of Esters

Treatment of the acids of Examples 1-188 with trifluoroacetic anhydride to provide the N-COCF$_3$ derivatives, followed by treatment with thionyl chloride to provide the N-COCF$_3$ acid chloride, followed by treatment with one of the following alcohols, followed by removal of the N-COCF$_3$ group with sodium hydroxide, by the method of Example 191, provides the corresponding esters of the starting acid.

Alcohols: methanol, ethanol, 2-methoxyethanol, butanol, pentanol, hexanol, cyclopentanol, cyclohexanol, 1,2-propanediol, 1,3-propanediol, ethylene glycol, glycerol, glycidol, glycolic acid, citric acid, tartaric acid, malic acid, methyl glycolate, 2-hydroxypropionic acid, 3-hydroxybutyric acid, 4-hydroxybutyric acid, glyceric acid, 3-diethylamino-1-propanol, 1-diethylamino-2- propanol, 1-dimethylamino-2-propanol, 3-dimethylamino-1-propanol, 2-diisopropylaminoethanol, 3-dimethylamino-1,2-propanediol, N-piperidineethanol, N,N-diethylethanolamine, benzyl alcohol, p-fluorobenzyl alcohol, p-bromobenzyl alcohol, p-chlorobenzyl alcohol, p-methoxybenzyl alcohol, m-chlorobenzyl alcohol, m-(trifluoromethyl)benzyl alcohol, p-carboxybenzyl alcohol, phenol, p-fluorophenol, p-bromophenol, p-chlorophenol, p-methoxyphenol, p-carboxyphenol, m-(trifluoromethyl)phenol, 4-cyanophenol, 3-hydroxypyridine, 2-chloro-3-hydroxypyridine, and 5-carboxy-3-hydroxypyridine.

EXAMPLE 193

Preparation of Amides

Treatment of the acids of Examples 1–188 with trifluoroacetic anhydride to provide the N-COCF$_3$ derivatives, followed by treatment with thionyl chloride to provide the N-COCF$_3$ acid chloride, followed by treatment with one of the amines of the list below, followed by removal of the COCF$_3$ with sodium hydroxide, by the method of Example 191, provides the corresponding amides of the starting acid.

Amides: ⊖-alanine, allylamine, N-allylaniline, allylcyclohexylamine, aminoacetonitrile, α-aminoacetophenone, 2-amino-1-butanol, 3-aminobutyric acid, 4-aminobutyric acid, 1-amino-1-cyclopentanemethanol, 2-amino-5-diethylaminopentane, N-(2-aminoethyl)morpholine, N-(2-aminoethyl)piperazine, N-(2-aminoethyl)piperidine, 2-amino-2-ethyl-1,3-propanediol, 2-(2-aminoethyl)pyridine, N-(2-aminoethyl)pyrrolidine, DL-4-amino-3-hydroxybutyric acid, 5-aminolevulinic acid, p-aminomethylbenzenesulfonamide, 2-amino-3-methyl-1-butanol, aminomethylcyclobutane, 4-(aminomethyl)cyclohexanecarbonitrile, 1-aminomethyl-1-cyclohexanol, aminomethylcyclopropane, 4-(aminomethyl)piperidine, 2-amino-2-methyl-1,3-propanediol, 2-amino-2-methyl-1-propanol, 2-(aminomethyl)-2-propanol, 2-aminomethylpyridine, 3-aminomethylpyridine, 4-aminomethylpyridine, 2-amino-1-phenylethanol, 2-amino-3-phenyl-1-propanol, 3-amino-3-phenylpropionic acid, 3-amino-1,2-propanediol, 1-amino-2-propanol, L-2-amino-1-propanol, 3-amino-1-propanol, N-(3-aminopropyl)diethanolamine, N-(3-aminopropyl)morpholine, 1-(3-aminopropyl)-2-pipecoline, N-(3-aminopropyl)-2-pyrrolidinone, 5-aminovaleric acid, bis-(2-ethoxyethyl)amine, bis-(2-methylallyl)amine, p-bromophenethylamine, 3-bromopropylamine, n-butylamine, sec-butylamine, tert-butylamine, 2-chlorobenzylamine, 3-chlorobenzylamine, 4-chlorobenzylamine, 2-chloroethylamine, 3-chloropropylamine, cyclobutylamine, cycloheptylamine, 1,3-cyclohexanebis(methylamine), cyclohexanemethylamine, cyclohexylamine, cyclopentylamine, cyclopropylamine, 3-(di-n-butylamineo)-propylamine, 1,5-dimethylhexylamine, α,4-dimethyl-3-hydroxyphenethylamine, 1,2-dimethylpropylamine, 1,2-diphenylethylamine, ethylamine, ethyl 3-aminobutyrate, ethyl 4-aminobutyrate, 2-(ethylamino)ethanol, 1-ethylpropylamine, 1-ethynylcyclohexylamine, m-fluorobenzylamine, p-fluorobenzylamine, 2-fluoroethylamine, furfurylamine, p-heptylamine, propylamine, m-iodobenzylamine, isoamylamine, isopropylamine, m-methoxybenzylamine, p-methoxybenzylamine, 2-methoxyethylamine, o-methoxyphenethylamine, p-methoxyphenethylamine, N-methyl-β-alaninenitrile, 2-methylallylamine, methylamine, methylaminoacetonitrile, 2-(methylamino)ethanol, 2-methylbenzylamine, 3-methylbenzylamine, 4-methylbenzylamine, 1-methylbutylamine, 4-methylcyclohexylamine, 1-norepinephrine, 4-phenylbutylamine, 1-phenylcyclopropanemethylamine, 2-phenylcyclopropylamine, N-phenylethylenediamine, α-phenylglycinol, 2-phenylglycinonitrile, phenylpropanolamine, 3-phenyl-1-propylamine, mono-propargylamine, propylamine, taurine, tetrahydrofurfurylamine, 1,2,3,4-tetrahydro-1-naphthylamine, 2-(p-tolyl)ethylamine, veratrylamine, m-xylylenediamine, m-aminobenzoic acid, p-aminobenzoic acid, o-aminobenzyl alcohol, m-aminobenzyl alcohol, p-aminobenzyl alcohol, 4-benzylpiperidine, 2,6-dimethylpiperidine, 2-ethylpiperidine, 3-hydroxypiperidine, 4-hydroxypiperidine, 2-methylpiperidine, 3-methylpiperidine, 4-methylpiperidine, 4-phenylpiperidine, piperidine, morpholine, hexamethyleneimine, heptamethylenimine, pyrrolidine, N-methylpiperazine, dl-alanine, hydrazine, N-acetylhydrazine, dl-valene, Δ$^3$-piperidine, dl-leucine, 2-aminoisobutyric acid, glycine, ethylglycinate.

EXAMPLE 194

Preparation of N-(p-[(cyclohexylmethyl)amino]benzoyl)benzamide 1.0 g. of sodium hydride (50% dispersion in mineral oil) under nitrogen is washed with hexane three times. To the dry sodium hydride is added 5 ml. of freshly distilled tetrahydrofuran. To this suspension is added a solution of 2.4 g. of benzamide in 5 ml. of tetrahydrofuran. After complete reaction (30 minutes) a solution of 0.9 g. p-[N-trifluoroacetyl-N-(cyclohexylmethyl)amino]benzoyl chloride in 3 ml. of tetrahydrofuran is added. After stirring at ambient temperature for 1 hour, the reaction mixture is poured into water and extracted twice with ether. The ether extracts are washed with water, brine, dried with sodium sulfate, and concentrated in vacuo. The residue is recrystallized from hot etheracetonitrile (1:1) to provide the amide.

EXAMPLE 195

Preparation of N-(p-[substituted amino]benzoyl)benzamides

Treatment of the N-COCF$_3$ acid halides (prepared from the corresponding acid of Examples 1–188 by the method of Example 191) with benzamide and sodium hydride by the method of Example 194 followed by removal of the N-COCF$_3$ group by the method of Example 191 is productive of the corresponding N-(p-[substituted amino]benzoyl)benzamides.

EXAMPLE 196

Preparation of 4-(8-cyclohexyloctylamino)benzoyl chloride hydrochloride

A cold solution of 25 g. of 4-(8-cyclohexyloctylamino)-benzoic acid in 500 ml. dimethoxyethane-methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield an orange, semi-crystalline mass.

EXAMPLE 197

4-[N-carbobenzyloxy-N-(8-cyclohexyloctyl)amino]benzoyl chloride

To 15 g. 4-(8-cyclohexyloctylamino)benzoic acid in 200 ml. warm chloroform is added 15 g. sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time to yield a viscous, orange oil.

EXAMPLE 198

Preparation of 1-{4-[N-(t-butyloxycarbonyl)-N-(8-cyclohexyloctyl)amino]benzoyl}imidazole To a solution of 10 g. 4-(8-cyclohexyloctylamino)benzoic acid in 100 ml. dioxane is treated with 4.0 g. t-butylazidoformate and 10 ml. pyridine. After stirring at room temperature for 18 hours, the protected amidoacid is precipitated from solution by addition of 150 ml. water. The product is collected and thoroughly dried. The crude product is dissolved in 200 ml. of a mixture consisting of methylene chloride/dimethoxyethane/pyridine (1:4:1), and to this is added 5.4 g. 1,1'-carbonyldiimidazole. The solution is stirred overnight at room temperature and the solvents are evaporated to yield the title compound as a thick, orange oil.

EXAMPLE 199

Preparation of 1-(methoxycarbonyl)propyl 4-(8-cyclohexyloctylamino)benzoate

To a solution of 10.0 g. 4-(8-cyclohexyloctylamino)benzoyl chloride hydrochloride in 200 ml. methylene chloride is dropwise added a solution of 3 g. methyl α-hydroxy butyrate and 5 g. triethylamine in 100 ml. ether. After 17 hours stirring at room temperature, the precipitae is filtered and washed with several portions of ether. The ether solution is washed with water, dried, and condensed to the crystalline title compound.

EXAMPLE 200

Preparation of 1-carboxyethyl 4-(8-cyclohexyloctylamino)-benzoate

A flask containing 10.0 g. 4-(8-cyclohexyloctylamino)-benzoic acid, 3.3 g. lactic acid, 500 mg. toluenesulfonic acid and 500 ml. toluene is equipped with a Soxhlet extractor charged with activated Å Linde molecular sieves. The solution is refluxed for 24 hours, during which time the Soxhlet extractor is charged twice more with fresh sieves. The hot solution is filtered and left to cool, whereupon the product separates as off-white crystals.

EXAMPLE 201

Preparation of O-[4-(8-cyclohexyloctylamino)benzoyl]malic acid

To a warm solution of N-carbobenzyloxy-4-(8-cyclohexyloctylamino)benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated ove 600 mg. 10% Pd(C) at 50 psi until hydrogen uptake stops. The catalyst is filtered, the solution is evaporated, and the residue is crystallized from acetic acid to yield the title compound as a tan, crystalline mass.

EXAMPLE 202

Preparation of 2-(ethoxycarbonyl)vinyl 4-(8-cyclohexyloctylamino)benzoate

To a mixture containing 4.3 g. 1-{4-[N-(t-butyloxycarbonyl)-N-(8-cyclohexyloctyl)amino]benzoyl}-imidazole, 50 ml. chloroform, and 50 l ml. 5 N sodium hydroxide is added 3 g. ethyl α-formyl acetate. The solution is vigorously sitrred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of the product.

EXAMPLE 203

Preparation of 3-O [4-(8-cyclohexyloctylamino)benzoyl]glyceric acid

To a solution of 3.6 g. glyceraldehyde and 2.44 g. 4-dimethylaminopyridine in an ice-water bath is added 11 mmoles of N-trifluoroacetyl-4-(8-cyclohexyloctylamino)benzyl chloride. After 4 hours, the product is partitioned between 50 ml. chloroform and 50 ml. water, and to the well stirred solution is added 2 g. bromine and 1 g. sodium hydroxide. After thin-layer chromatography at intervals shows oxidation to be complete, the mixture is stirred 2 hours at 20° C. and the layers are separated. The organic layer is evaporated and the residue is crystallized from acetic acid to yield the title compound as a cream-colored, oily solid.

EXAMPLE 204

Preparation of 4-chlorophenyl 4-(8-cyclohexyloctylamino)benzoate

To a solution of 6.4 g. 4-chlorophenol and 7.6 g. triethylamine in 500 ml. methylene chloride is added 10.4 g. 4-(8-cyclohexyloctylamino)benzoyl chloride hydrochloride in 250 ml. methylene chloride. After four hours at reflux, the solution is cooled, washed with water and dilute phosphoric acid, and dried. After passing the solution through a column of alumina, the solvent is evaporated an the residue is crystallized from diisopropyl ether.

EXAMPLE 205

Preparation of 2-tetrahydropyranyl 4-(8-cyclohexyloctylamino)benzoate

A mixture of 7 g. 4-(8-cyclohexyloctylamino)benzoic acid, 2 g. 2,3-dihydropyran and 100 mg. anhydrous p-toluenesulfonic acid in 50 ml. toluene is stirred at room temperature for 20 hours. The solution is washed with saturated sodium bicarbonate, dried, and condensed. The residue is crystallized from methylcyclohexane to white crystals.

EXAMPLE 206

Preparation of 3-pyridyl 4-(8-cyclohexyloctylamino)benzoate

A 6 g. sample of 4-(8-cyclohexyloctylamino)benzoic acid and 2.7 g. 1,1'-carbonyldiimidazole in 50 ml. dry tetrahydrofuran is stirred for 2 hours. Then, 1.58 g. 3-hydroxypyridine and a trace of sodium hydride catalyst is added and the reaction is refluxed for 3 hours. The solution is cooled, filtered, and evaporated. The product is crystallized from isopropanol.

EXAMPLE 207

2,3-Dihydroxypropyl 4-(8-cyclohexyloctylamino)benzoate

A solution of 7.34 g. of 4-(8-cyclohexyloctylamino)benzoic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield the product.

EXAMPLE 208

2,3-Dihydroxypropyl 4-(8-cyclohexyloctylamino)benzoate

A solution of 11.8 g. of 4-(8-cyclohexyloctylamino)benzoic acid, 1.00 g. of glycerol, and 5.35 ml. of boron trifluoride etherate in 200 ml. of toluene is stirred under reflux for 48 hours. The solution is treated with an additional 5.35 ml. of boron trifluoride etherate and refluxing is continued for 120 hours. Dilution with water and methylene chloride followed by filtration affords the product as a white solid.

EXAMPLE 209

2,3-Epoxypropyl 4-(8-cyclohexyloctylamino)benzoate

A mixture of 89.0 g. of epichlorohydrin, 92.0 g. of sodium 4-(8-cyclohexyloctylamino)benzoate, and 350 ml. of hexamethylphosphoramide is stirred at 105° C. for 5 hours, allowed to cool, and poured into 1.0 liter of water. The white solid is collected by filtration, recrystallized from acetonitrile and then from hexane-methylene chloride to yield the product.

EXAMPLE 210

Preparation of N-[4-(8-cyclohexyloctylamino)benzoyl]-piperidide

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-(8-cyclohexyloctylamino)benzoyl chloride hydrochloride in 50 ml. of ether. The solution is warmed to room temperature and maintained there for two hours. The solution is heated to reflux for an additional 2 hours at which time the reaction was complete. The solution is cooled, extracted twice with 100 ml. portions of water and dried over MgSO$_4$. The solvent is removed in vacuo and the solid is recrystallized from ether to yield the product.

EXAMPLE 211

Preparation of ethyl 4-(8-cyclohexyloctylamino)hippurate

A solution of 18.0 g. of 4-(8-cyclohexyloctylamino)benzoyl chloride hydrochloride in 100 ml. of dioxane is added to freshly prepared ethyl glycinate in 300 ml. of CH$_2$Cl$_2$ containing 1 g. of dimethylaminopyridine and 10 ml. of triethylamine. After 16 hours at room temperature the reaction mixture was refluxed for 2 hours, cooled and filtered. The mother liquor is extracted with water and 10% hydrochloric acid. The solution is dried over magnesium sulfate and concentrated in vacuo to an amber liquid. A 6 g. sample is pre-absorbed on 30 g. of silica III and placed on 250 ml. of alumina and eluted with ether giving 4.2 g. of solid. Thin-layer chromatography (hexane:ethylacetate, 3:1) indicates three components so this material (3 g.) is chromatographed on silica giving a solid which is recrystallized from acetonitrile to yield the product.

EXAMPLE 212

Preparation of N-[4-(8-cyclohexyloctylamino)benzoyl]glycine

A mixture of 26.4 g. of ethyl N-[4-(8-cyclohexyloctylamino)benzoyl]glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone to yield the product.

EXAMPLE 213

Preparation of p-(8-cyclohexyloctylamino)-N-(phenylsulfonyl)-benzamide

A solution of 31.4 g. of benzenesulfonamide in 250 ml. dry dimethylacetamide is added dropwise, with stirring and cooling, to a suspension of 5.5 g. of sodium hydride in 100 ml. of dry dimethylacetamide over 30 minutes at room temperature. Stirring is continued for a further 30 minutes. In the meantime, a mixture of 36.2 g. of p-(8-cyclohexyloctyl)aminobenzoic acid in 1200 ml. of methylene chloride, 300 ml. of dimethoxyethane, and 40 ml. of thionyl chloride is refluxed for 1 hour and 15 minutes. The solution is evaporated to an oil.

To the resulting oily residue of p-(8-cyclohexyloctyl)aminobenzoyl chloride hydrochloride is added, in one portion, the previously prepared mixture of sodium benzenesulfonamide in dimethylacetamide. The mixture is stirred for 30 minutes, without cooling, and is then filtered through a bed of diatomaceous earth. The filtrate is poured into 2 l. of water, and 250 ml. of saturated sodium chloride solution is added to coagulate the precipitate. The mixture is filtered and the product is washed with water and partially air dried. The product is dissolved in methylene chloride, the mixture is filtered through diatomaceous earth, and brine is added to break the emulsion. The layers are separated, the organic phase is dried over anhydrous sodium sulfate and filtered through a bed of 300 g. of hydrous magnesium silicate. The product is eluted with an additional 3 l. of methylene chloride. The first approx. 1 l. of filtrate is set aside and the remainder is evaporated to dryness. The residue is crystallized three times from toluene to yield the product.

EXAMPLE 214

Preparation of 3-[4-(8-cyclohexyloctylamino)benzoyl]carboxythiazolidine

One-tenth mole of 4-(8-cyclohexyloctylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is crystallized from acetonitrile. By means of the alkaline hydrolysis method of Example 1, the ethyl ester is converted to the subject carboxylic acid. This acid is also prepared using the procedure of this Example except that the acylation of the thiazolidine-4-carboxylic acid is carried out in aqueous acetone sodium bicarbonate solution.

EXAMPLE 215

Preparation of N-[4-(8-cyclohexyloctylamino)benzoyl]piperide

To a warm solution of 4-[N-carbobenzoyloxy-N-8-(cyclohexyl)octylamino]benzoyl chloride and 1.3 g. of triethylamine in 100 ml. ether is added 1.2 g. of piperidine. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% Pd-on-carbon at 50 psi. until hydrogen up-take stops. The catalyst is filtered. The solution is evaporated, and the residue is crystallized from acetic acid to yield the title compound as a crystalline mass.

EXAMPLE 216

Preparation of 4-[N-(8-cyclohexyloctyl)-amino]-N-2,3-dihydroxypropylbenzamide To a mixture containing 4.3 g. of 1-{4-[N-(t-butyloxycarbonyl)-N-(8-cyclohexyloctyl)amino]benzoyl}-imidazole, 50 ml. of chloroform and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals of the product.

EXAMPLE 217

Preparation of N-[4-(8-cyclohexyloctylamino)benzoyl]-2-aminoethanesulfonic acid To a stirred solution of 2.50 g. of taurine and 5.6 ml. of triethylamine in 22.5 ml. of water is added 5.55 g. of N-{p-[2,2,2-trifluoro-N-(8-cyclohexyloctyl)acetamido]-benzoyloxy}succinimide as a solution in 45 ml. of ethanol. After 24 hours, the mixture is treated with 20 ml. of 2.0 M sodium hydroxide and 25 ml. of water. After stirring for 10 min., the mixture is acidified with dilute hydrochloric acid, and the crude product is collected by filtration. Recrystallization affords the title compound as a white solid.

EXAMPLE 218

Preparation of 4-[(8-cyclohexyloctyl)amino]-N-3-bromopropylbenzamide.

To a slurry of 21.80 g. of 2-bromopropylamine hydrobromide in 200 ml. of glyme at 3° C. is added a solution of 23.96 g. of 4-(8-cyclohexyloctylamino)benzoyl chloride hydrochloride in 65 ml. of glyme, concurrently with 26 ml. of triethylamine diluted to 39 ml. with glyme. The solution is warmed to reflux and 0.2 g. of 4-dimethylaminopyridine is added. The solution is heated for four hours and cooled overnight. The solid is removed by filtration and the filtrate diluted with 200 ml. of water. The precipitate is collected and crystallized from cyclohexane. The solid is recrystallized from acetonitrile to yield the product.

EXAMPLE 219

Preparation of 2-[4-(8-cyclohexyloctylamino)phenyl]-5,6-dihydro[4H]-1,3-oxazine To 0.4 g. of NaH in 100 ml. of glyme is added 2.14 g. of N-(3-bromopropyl)-4-(8-cyclohexyloctylamino)benzamide and 12 ml. of triethylamine. The turbid solution is heated under reflux for 30 hours. The solution is diluted with 100 ml. of water and cooled overnight. The solid is collected, washed with water and dried to yield 2 g. of solid which gave a negative silver nitrate test and halogen flame test. This solid is recrystallized from cyclohexane to yield the product.

EXAMPLE 220

Preparation of 2-[4-(8-cyclohexyloctylamino)phenyl]oxazoline

To a slurry of 15 g. of 2-bromoethylamine hydrobromide in 150 ml. of glyme are added simultaneously solutions of 31 g. of 4-(8-cyclohexyloctylamino)benzoyl chloride hydrochloride in 60 ml. of glyme and 50 ml. of triethylamine (dropwise). After the addition of 0.5 g. of 4-dimethylaminopyridine the "solution" is stirred at room temperature overnight, refluxed for one hour and filtered. The solid is dried and partitioned between methylene chloride and water. The layers are separated and the methylene chloride solution is dried over magnesium sulfate, concentrated to a volume of about 100 ml., and diluted with an equal volume of hexane. The product is collected by filtration and recrystallized from cyclohexane and then from acetonitrile and methylene chloride/hexane to yield the product.

I claim:

1. A compound of the formula:

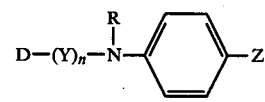

wherein Z is a moiety of the formula:

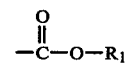

wherein $R_1$ is selected from the group consisting of phenyl, benzyl, 3-pyridyl, pyridylmethyl and tetrahydropyranyl;

R is selected from the group consisting of hydrogen and methyl;

n is either zero or one;

Y is a divalent radical selected from the group consisting of unbranched or branched $C_1$-$C_{13}$ alkylene or alkenylene and is either unsubstituted or substituted with $C_1$-$C_4$ alkyl group;

and D is selected from the group consisting of $C_3$-$C_{16}$ cycloalkyl or $C_4$-$C_{17}$ cycloalkenyl and is either unsubstituted or substituted with $C_1$-$C_{13}$ alkyl, $C_4$-$C_8$ cycloalkyl, decahydronaphthyl, methylene, ethylidene, or isopropylidine group;

with the proviso that the total number of carbon atoms in D and Y shall not exceed twenty; and with the further proviso that when n is 1, D is not an unsubstituted cyclopropyl nor a cyclopropyl substituted with $C_1$-$C_{13}$ alkyl;

and the pharmaceutically acceptable non-toxic acid-addition and cationic salts thereof.

2. A compound of the formula:

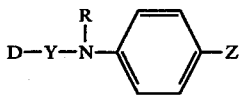

wherein Z is a moiety of the formula:

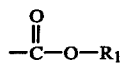

wherein $R_1$ is selected from the group consisting of phenyl, benzyl, 3-pyridyl, pyridylmethyl, and tetrahydropyranyl;

R is hydrogen,

Y is a divalent radical selected from the group consisting of branched or unbranched $C_1$-$C_{13}$ alkylene or alkenylene and is either unsubstituted or substituted with $C_1$-$C_4$ alkyl;

D is a moiety selected from the group consisting of $C_3$-$C_8$ cycloalkyl and is either unsubstituted or substituted with $C_1$-$C_3$ alkyl, $C_3$-$C_8$ cycloalkyl which is either unsubstituted or substituted with a $C_5$-$C_7$ cycloalkyl, or decahydronaphthyl; with the proviso that D is not an unsubstituted cyclopropyl nor a cyclopropyl subsituted with $C_1$-$C_{13}$ alkyl;

and the pharmaceutically acceptable non-toxic acid-addition and cationic salts thereof.

3. A compound according to claim 1, wherein R, D and Z are as previously defined; and Y is a divalent radical selected from the group consisting of straight-chain $C_1$-$C_{13}$ alkylene.

4. A compound according to claim 3, wherein R, Z and Y are as previously defined; and D is a moiety selected from the group consisting of $C_5$-$C_8$ cycloalkyl.

5. A compound according to claim 4, wherein R, D and Z are as previously defined; and Y is a divalent radical selected from the group consisting of straight-chain $C_6$-$C_8$ alkylene.

6. A compound of the formula:

wherein R is selected from the group consisting of phenyl, benzyl, 3-pyridyl pyridylmethyl, and tetrahydropyranyl; D is a moiety selected from the group consisting of $C_4$-$C_7$ cycloalkyl and is either unsubstituted or substituted with $C_4$-$C_7$ cycloalkyl, and decahydronaphthyl unsubstituted or substituted with $C_1$-$C_4$ alkyl, and the pharmaceutically acceptable non-toxic, acid-addition and cationic salts thereof.

7. A compound according to claim 6, wherein R is as previously defined; and D is selected from the group consisting of $C_5$-$C_6$ cycloalkyl unsubstituted or substituted with $C_5$-$C_6$ cycloalkyl, and decahydronaphthyl unsubstituted or substituted with $C_1$-$C_4$ alkyl.

8. A compound of the formula:

wherein R is selected from the group consisting of phenyl, benzyl, 3-pyridyl, pyridylmethyl, and tetrahydropyranyl; D is a moiety selected from the group consisting of $C_3$-$C_{16}$ cycloalkyl unsubstituted or substituted with $C_1$-$C_5$ alkyl; and the pharmaceutically acceptable non-toxic acid-addition and cationic salts thereof.

9. A compound according to claim 8, wherein R is as previously defined; and D is selected from the group consisting of $C_3$-$C_6$ cycloalkyl unsubstituted or substituted with $C_1$-$C_5$ alkyl.

10. A compound according to claim 8, wherein R is as previously defined; and D is selected from the group consisting of $C_3$-$C_{16}$ cycloalkyl.

11. A compound according to claim 10, wherein R is as previously defined; and D is selected from the group consisting of $C_5$-$C_{12}$ cycloalkyl.

12. A compound of the formula:

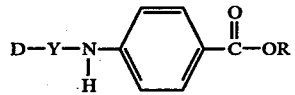

wherein R is selected from the group consisting of phenyl, benzyl, 3-pyridyl, pyridylmethyl and tetrahydropyranyl; D is a moiety selected from the group consisting of $C_4$-$C_9$ cycloalkenyl, $C_4$-$C_9$ cycloalkenyl substituted with $C_1$-$C_2$ alkyl, and $C_5$-$C_8$ cycloalkyl substituted with a methylene moiety and/or $C_1$-$C_2$ alkyl; Y is a divalent radical selected from the group consisting of branched or unbranched $C_1$-$C_{13}$ alkylene or alkenylene and is either unsubstituted of substituted with $C_1$-$C_2$ alkyl; and the pharmaceutically acceptable non-toxic acid-addition and cationic salts thereof.

13. A compound according to claim 12, wherein R is as previously defined; and D is selected from the group consisting of $C_5$-$C_8$ cycloalkenyl unsubstituted or substituted with $C_1$-$C_2$ alkyl; and Y is a divalent radical selected from the group consisting of $C_1$-$C_{13}$ alkylene.

14. A compound according to claim 13, wherein R and D are as previously defined; and Y is a divalent radical selected from the group consisting of $C_4$-$C_{13}$ alkylene.

15. A compound according to claim 14, wherein R and Y are as previously defined; and D is selected from the group consisting of $C_5$-$C_6$ cycloalkenyl.

16. A compound according to claim 12, wherein R is as previously defined; and D is selected from the group consisting of $C_5$-$C_8$ cycloalkyl substituted with a methylene moiety and unsubstituted or substituted with $C_1$-$C_2$ alkyl; and Y is a divalent radical selected from the group consisting of $$-CH_2- \quad \text{and} \quad -\underset{\underset{CH_3}{|}}{CH}-.$$

17. A compound of the formula:

wherein R is selected from the group consisting of phenyl, benzyl, 3-pyridyl, pyridylmethyl, and tetrahydropyranyl; D is a moiety selected from the group consisting of $C_4$-$C_{17}$ cycloalkenyl unsubstituted or substituted with $C_1$-$C_4$ alkyl, and $C_4$-$C_{10}$ cycloalkyl substituted with a moiety selected from the group consisting of methylene, ethylidene and isopropylidene and/or $C_1$-$C_3$ alkyl; and the pharmaceutically acceptable non-toxic acid-addition and cationic salts thereof.

18. A compound according to claim 17, wherein R is as previously defined; and D is a moiety selected from the group consisting of $C_4$-$C_{17}$ cycloalkenyl, substituted with $C_1$-$C_4$ alkyl.

19. A compound according to claim 18, wherein R is as previously defined; and D is a moiety selected from the group consisting of $C_5$-$C_{17}$ cycloalkenyl.

20. A compound according to claim 19, wherein R is as previously defined; and D is a moiety selected from the group consisting of $C_6$-$C_{15}$ cycloalkenyl.

21. A compound according to claim 17, wherein R is as previously defined; and D is a moiety selected from the group consisting of $C_4$-$C_{10}$ cycloalkyl substituted with methylene, ethylidene or isopropylidene.

22. A compound according to claim 21, wherein R is as previously defined; and D is a moiety selected from the group consisting of $C_5$-$C_{10}$ cycloalkyl substituted with methylene.

23. The compound according to claim 1, 4-chlorophenyl 4-(8-cyclohexyloctylamino)benzoate.

24. The Compound according to claim 1, 3-pyridyl 4-(8-cyclohexyloctylamino)-benzoate.

25. The method of inhibiting atherosclerotic lesion development in a mammal comprising the administration of an effective lesion-development inhibiting amount of a compound of claim 1.

26. The method of claim 25, wherein said compound is administred to provide a daily dosage of from about one mg. to about 250 mg. per kilogram of body weight of said mammal.

27. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 1.

28. The method of inducing regression of atherosclerotic lesion development in a mammal comprising administering to said mammal an effective lesion-regressive amount of a compound of claim 1.

29. The method of claim 28, wherein said compound is administered to provide a daily dosage of from about one mg. to about 250 mg. per kilogram of body weight of said mammal.

30. The method of treating hyperlipidemia and hyperlipoproteinemia and/or altering the lipotrotein pattern in a mammal comprising administration to said mammal of an effective lipid-altering amount of a compound of claim 1.

* * * * *